United States Patent [19]

Goel

[11] Patent Number: 4,783,518

[45] Date of Patent: Nov. 8, 1988

[54] RAPID CURING EPOXY COMPOSITIONS

[75] Inventor: Anil B. Goel, Worthington, Ohio

[73] Assignee: Ashland Oil, Inc., Ashland, Ky.

[21] Appl. No.: 101,718

[22] Filed: Sep. 28, 1987

[51] Int. Cl.$^4$ .............................................. C08G 59/68
[52] U.S. Cl. ....................................... 528/90; 528/94;
528/341; 528/361; 528/407
[58] Field of Search .................. 528/90, 94, 341, 361, 528/407

[56] References Cited

U.S. PATENT DOCUMENTS

| | | | |
|---|---|---|---|
| 3,361,715 | 1/1968 | Vogt et al. | 528/90 |
| 3,642,649 | 2/1972 | Green et al. | 252/182 |
| 3,660,354 | 5/1972 | Velzmann | 528/90 X |
| 4,161,575 | 7/1979 | Seymour et al. | 528/90 |
| 4,600,763 | 7/1986 | Goel | 528/117 X |
| 4,696,992 | 9/1987 | Goel | 528/109 X |

*Primary Examiner*—Earl Nielsen
*Attorney, Agent, or Firm*—John F. Jones

[57] ABSTRACT

A rapid curing composition comprising a mixture of (A) a polyepoxide and an amine curing agent and (B) a novel thiocyanate salt of the reaction product of an alkylene polyamine, such as ethylene diamine, and a bicyclic amide acetal and a method for curing said composition are described.

20 Claims, No Drawings

RAPID CURING EPOXY COMPOSITIONS

This invention relates to the use of cure accelerators for the rapid curing of epoxy resin-amine materials said cure accelerators comprising the thiocyanate salts of the reaction products of bicyclic amide acetals and alkylene polyamines and to the curable compositions resulting from the combination of these cure accelerators with said epoxy resin-amine materials.

A variety of aromatic and aliphatic polyamines (primary, secondary, mixed primary and secondary, and combinations of these with tertiary amines) and amido amines therefrom have been known as curing agents for epoxy resin materials. In order to improve the cure speed of the amine curing of epoxy compositions, various types of cure accelerators include (1) tertiary amines, (2) phenolics, (3) quaternary ammonium salts of strong acids, (4) metal salts of carboxylic acids, (5) boron trifluoride-amine and boron trifluoride-phenol complexes, and (6) mercaptans and thioether alcohols have been used in the prior art. The use of thiocyanate salts of the reaction products of bicyclic amide acetals with alkylene polyamines as cure accelerators in the epoxy resin-amine curing systems has not previously been described.

In order to improve the cure speed of the polyepoxide-polyamine curing systems, various types of cure accelerators have been used including tertiary amino group containing materials, phenolics, quaternary ammonium salts of strong acids and carboxylic acids, metal salts of carboxylic acids, boron trifluoride-amine complexes and boron trifluoride-phenol complexes, mercaptans, thioether alcohols and thiocarbamic acids. In this regard, see the article by Mika in "Epoxy Resins Chemistry and Technology," edited by May and Tanaka, Marcel Dekker, Inc., New York, 1973. U.S. Pat. Nos. 3,265,664 and 3,271,350 describe the use of guanamine as cure accelerators. U.S. Pat. Nos. 3,291,776 and 3,821,166 describe the use of thioether and mercaptans. U.S. Pat. No. 3,637,591 describes the use of neutral esters of a phosphorus acid for this purpose. U.S. Pat. No. 2,909,494 describes the use of boron trifluoride-amine, U.S. Pat. No. 4,554,342 describes the use of trihydrocarbyl sulfonium salts and U.S. Pat. No. 4,110,313 describes the use of dithiocarbamate salts. U.S. Pat. No. 4,195,153 describes the use of an amino alcohol as an accelerator for the amine curing of epoxy resins. U.S. Pat. No. 3,903,048 describes the use of dimethyl dithiocarbamic acid dimethyl ammonium salt, bis(dimethyl thiocarbamyl) sulfide, tetramethylthiuram disulfide and the like as catalyst systems for lowering epoxy resin cure temperatures when cured with dicyandiamide. The use of a tertiary amine salt of thiocyanic acid as an amine cure accelerator for epoxy resins has been shown in U.S. Pat. Nos. 3,642,649 and 4,161,575. Quaternary ammonium (tetraalkylammonium) thiocyanate as accelerators for epoxy resins has been shown in U.S. Pat. No. 3,660,354. The use of alkali and alkaline earth metal thiocyanate salts with aminoethylpiperazine as curing agent for epoxy resins has been shown in Japanese Pat. No. 597823 [Chem. Abstr. 101 (20) 1723927]. Similarly, epoxy curing with polyamine/thiourea has been described in Japanese Pat. No. 48092437.

Thus, it is quite apparent that the rapid curing of epoxy resins has been the subject of much industrial interest. Although the prior art cure accelerators improve the cure speed of epoxy resins when cured with amine curing agents, such accelerators are often associated with some limitations. For instance, accelerators (such as boron trifluoride-amine complexes and boron trifluoride-phenol complexes) are corrosive and the esters of phosphorus acid and metal carboxylates (such as stannous octoate) are moisture sensitive. Some of the prior art accelerators are not very efficient and promote acceleration only mildly. In addition to this, most prior art accelerators either copolymerize with the epoxy resins (for instance, phenolics, mercaptans, thiocarbamic acids) or catalyze the homopolymerization of epoxy resins. Representative of such catalysts are tertiary amines, boron trifluoride-amine salts and metal carboxylates.

It is an objective of this invention to provide rapid curing epoxy resin compositions cured with amine hardeners using a new class of cure accelerators which are free from the above-described limitations often associated with the prior art accelerators. The novel accelerators of this invention do not, per se, cure epoxy resins.

I have discovered that the thiocyanate salts of the reaction products of a bicyclic amide acetal and an alkylene polyamine are excellent cure accelerators for the curing of epoxy resin-amine curing agent mixtures. The amine curing agents include amido amines which are formed by the amidation of a polyamine with a carboxylic acid.

The bicyclic amide acetals useful in this invention are those having the Formula I

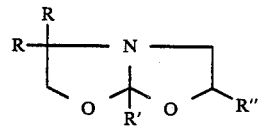

wherein R, R' and R" independently represent a hydrogen, an alkyl group having from 1 to 20 carbon atoms, an alkyl ether group having from 1 to 20 carbon atoms, an aryl group having from 5 to 20 carbon atoms, an aryl ether group having from 6 to 20 carbon atoms, an alkaryl group having from 7 to 20 carbon atoms or an alkaryl ether group having from 7 to 20 carbon atoms.

The rapid curing epoxy resin compositions of the present invention are preferably mixtures of two main components comprising a first component containing at least one polyepoxide (or epoxy resin) as hereinafter defined and a second component comprising an amine hardener and an accelerator which is the thiocyanate salt of the reaction product of a bicyclic amide acetal and an alkylene polyamine. The thiocyanate salt is preferably prepared by reaction of ammonium thiocyanate with the reaction product of the bicyclic amide acetal and the polyamine. The amine hardener or curing agent can be a polyamine (primary, secondary, tertiary amino group containing compound or mixed primary amine, secondary amine tertiary amino group containing compound) and/or amido amines obtained by amidation of these amines with carboxylic acids. Either or both of the foregoing essential components may also contain modifiers, flexibilizers, diluents, fillers, pigments, and the like as are known to those skilled in the art.

The alkylene polyamines useful in this invention for formation of the reaction products with bicyclic amide acetals preferably are those of Formula II

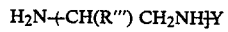

wherein R''' represents hydrogen or a methyl group, Y represents hydrogen or an aminoalkyl group having from 2 to 6 carbon atoms and n represents 1 or 2.

Representative alkylene polyamines of this type II include ethylene diamine, propylene diamine, diethylene triamine, dipropylene triamine triethylene tetramine, tripropylene tetramine, and the like.

Epoxy resins or polyepoxides useful in the practice of this invention include those disclosed in U.S. Pat. Nos. 2,500,600 and 2,324,483 which are incorporated herein by reference. Preferred in this invention are 1,2-epoxy compounds having an epoxide equivalence greater than 1, that is to say, compounds containing more than one group of the formula:

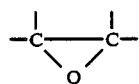

The 1,2-epoxide groups may be either terminal or inner ones. Particularly suitable terminal 1,2-epoxide groups are 1,2-epoxy ethyl or 1,2-epoxy propyl groups. The latter may be linked to an oxygen atom, that is to say, they are glycidyl ether or glycidyl ester groups. Compounds with inner epoxide groups usually contain the 1,2-epoxide group in an aliphatic chain or in a cycloaliphatic ring.

As epoxy compounds containing an inner 1,2-epoxy group there are suitable epoxidized diolefins, dienes, or cyclic dienes, such as 1,2,5,6-diepoxy hexane, 1,2,4,5-diepoxy cyclohexane, dicyclopentadiene diepoxide, dipentenediepoxide, vinyl cyclohexene diepoxide, epoxiized diolefinically unsaturated carboxylic acid esters, such as methyl-9,10,12,13-diepoxy stearate or the dimethyl ester of 6,7,10,11-diepoxyhexadecane-1,16-dicarboxylic acid. Furthermore, there may be mentioned epoxidized nono-, di-, or polyalcetals containing at least one cycloaliphatic 5-membered or 6-membered ring, to which at least two 1,2-epoxidized groups are linked.

A widely used class of polyepoxides which can be used in the present invention are the epoxy polyethers obtained by reacting a halogen containing epoxide or dihalohydrin, such as epichlorohydrin, epibromohydrin, 3-chloro-1,2-epoxyoctane, and the like with either a polyhydric phenol or a polyhydric alcohol.

The reaction of ammonium thiocyanate with the reaction products of bicyclic amide acetals and alkylene polyamines at moderately elevated temperatures (from about 60 to about 150 degrees C.) proceeds readily with the evolution of ammonia to yield products which are the cure accelerators of this invention which show a strong infrared spectral band at about 2060 cm$^{-1}$ which is characteristic of the presence of the thiocyanate group in the product. These new cure accelerators by themselves show extremely poor reactivity towards the curing of epoxy resins. However, when the cure accelerators of this invention are used in admixture with commonly known amine and/or amido amine curing agents for epoxy resins, rapid curing of the epoxy resin composition occurs at ambient temperatures as well as at low to moderately elevated temperatures (about 60 degress C. to about 150 degrees C.). The accelerators embodied in this invention accelerate the curing of epoxy resins in admixture with amine hardeners to such an extent that small amounts (from about 1% to about 10% by weight of the accelerator based on the weight of the hardener component) is required in order to reduce the cure time several fold. For instance, the reaction of a liquid diglycidyl ether of Bisphenol-A with aminoethylpiperazine (20% by weight of the total composition) which requires approximately 50 minutes at room temperature to give a gelled product, when carried out in the presence of about 5% (by weight based on the total epoxy resin/amine composition) of the product of the reaction of a bicyclic amide acetal and 1,2-propylene diamine/ammonium thiocyanate, the curing occurs within 4 minutes of mixing at room temperature (about 12 times faster reaction). Other important features of the accelerators of this invention are their ability to promote the cure acceleration of epoxy resins when cured with amine hardeners containing other conventional known cure accelerators, such as phenolics, mercaptans, and the like. The degree of cure speed acceleration for individual catalysts, as expected, may depend on the type of amine curing agent used.

Amine hardeners for the curing of polyepoxides are well known in the art and they include mono-, di-, and polyamines containing primary amine groups, secondary amine groups, mixed primary and secondary amine groups and combinations of these with tertiary amine groups and the amido amines prepared from such amines by amidation with carboxylic acids. These amines and amido amines may also contain other functionalities such as ether, thioether, hydroxyl, urea and the like groups. Typical of such amines are butylamine, dodecylamines, cyclohexylamine, ethylene diamine, diethylene triamine, triethylene tetramine, tetraethylene pentamine and the like, propylene diamine, dipropylene triamine and the like, bis caminomethyl)cyclohexane, triethyl amine, tributylamine, triethylene diamine, imidazolines, imidazoles, imidazines, hexamethylene diamine, isophorone diamine, aminoethylpiperazine, bis-(aminopropyl) piperazine, piperidine, piperazine, morpholine, dimer acid diamine, alkanolamines such as ethanolamine, diethanolamine, N-alkyl alkanolamines and poly(alkylene ether) polyamines of molecular weights up to 10,000. Useful amido amine curing agents include those obtained by the reaction of di- or polyalkylene amines such as ethylene diamine, diethylene triamine, and the like with higher carboxylic acids such as linoleic acid and fatty acids.

The rapid curing epoxy resin compositions resulting from mixing of the two components of this invention can be used in many applications such as coatings, adhesives, reaction injection molding (RIM), reinforced plastics, composites, potting and tooling compounds, injection molding, sheet molding compounds (SMC), and the like.

The accelerators of this invention may be encapsulated in either thermoplastic materials or by reacting with reactive molecules such as isocyanate, epoxide and other techniques known in the prior art.

This invention is further illustrated in the following representative examples.

EXAMPLE 1

To a 100 ml round bottom flask containing a magnetic stirring bar and equipped with a thermometer with a temperature controller and nitrogen gas inlet and outlet was charged 13g of a bicyclic amide acetal of Formula I wherein R and R'' represent hydrogen and R' represents a methyl group and 7.4g of 1,2-diaminopropane. The resulting mixture was heated at 110 degrees C. with stirring and under a nitrogen atmosphere for 15 minutes. GLC analysis of the resulting solution showed complete disappearance of the starting amide acetal. The temperature was reduced to 65 degrees C. and 15.2g of powdered ammonium thiocyanate was added. A rapid reaction occurred with ammonia gas evolution. The reaction was continued for 30 minutes at 110 degrees C. and the resulting solution was degassed under reduced pressure. The infrared spectrum of the liquid product showed the presence of a strong band at 2060 cm$^{-1}$ showing the product was a thiocyanate salt. The liquid product was used as a cure accelerator "A" for the amine curing of epoxy resin/amine hardener compositions. Typically, 0.5g of this liquid accelerator was mixed with 2.5g of aminoethylpiperazine to give a hardener component which was mixed with 12g of liquid diglycidyl ether of Bisphenol-A (epoxy equivalent weight of 180–195, DGEBPA) at room temperature. The resulting mixture was found to gel within four minutes with an exothermic reaction to give a thermoset solid polymer.

EXAMPLE 2

This comparative example which is outside the scope of this invention demonstrates that without the use of the cure accelerators of this invention the conventional amine curing agents such as aminoethylpiperazine containing epoxy resin materials cure at a much slower rate. In a typical experiment, a mixture of the two component epoxy resin composition containing DGEBPA (12g) and aminoethylpiperazine (3g) when kept at room temperature resulted in gelation in about 50 minutes to give a solid polymer. In another experiment, 12g of DGEBPA was mixed with 2.5g of aminoethylpiperazine and 0.5g of the bicyclic amide acetal described in Example 1. Gelation occurred in about 52 minutes at room temperature. In yet another experiment, 12g of DGEBPA was allowed to react with 2.5g of aminoethylpiperazine and 0.5g of 1,2-diaminopropane. This mixture was found to cure at room temperature in 45 minutes. In another experiment, 12g of DGEBPA was mixed with 2.5g of aminoethylpiperazine and 0.5g of the reaction product of 13g of the bicyclic amide acetal of Example 1 and 7.4g of 1,2-diaminopropane which had not been treated with ammonium thiocyanate. The resulting mixture was found to gel at room temperature in 20 minutes.

EXAMPLE 3

The procedure of Example 1 was followed using 13g of the bicyclic amide acetal, 1.6g of ethylene diamine and 7.6g of ammonium thiocyanate. The resulting product was used as cure accelerator "B" in the amine curing of epoxy resin compositions. Typically, 2.5g of aminoethylpiperazine was mixed with 0.5g of this accelerator and the resulting hardener component was then mixed with 12g of liquid DGEBPA. The resulting mixture was found to gel at room temperature within six minutes and 30 seconds.

EXAMPLES 4–24

Various epoxy resin compositions containing different types of amine hardeners and the cure accelerators of Examples 1 and 3 were prepared by the following procedure of Example 1 and were then tested for cure speed at room temperature and in some cases, at higher temperatures. For comparison purposes, experiments were carried out using amine hardeners without any added cure accelerators and these Examples (5, 7, 9, 11 and 15 are outside the scope of the present invention). The ingredients used and results obtained are given in the following Table.

TABLE

| | Epoxy Composition | | | | |
|---|---|---|---|---|---|
| Example No. | Epoxy Resin (g) | Amine Hardener (g) | Cure Accelerator (g) | Reaction Temp (°C.) | Gel Time (Minutes) |
| 4 | DGEBPA (12) | DETA (2.5) | A (0.5) | RT | 10.5 |
| 5 | (12) | DETA (3) | NONE | RT | 45 |
| 6 | (12) | TETA (2.5) | A (0.5) | RT | 11 |
| 7 | (12) | TETA (3) | NONE | RT | 69 |
| 8 | (12) | EDA (2.5) | A (0.5) | RT | 10 |
| 9 | (12) | EDA (3) | NONE | RT | 42 |
| 10 | (12) | TREN (2.5) | A (0.5) | RT | 8 |
| 11 | (12) | TREN (3) | NONE | RT | 55 |
| 12 | (10) | T403 (4) | A (0.5) | 115 | 3.5 |
| 13 | (10) | T403 (4) | NONE | 115 | 6 |
| 14 | (10) | D400 (3) + AEP (1) | A (0.5) | 115 | 1.8 |
| 15 | (10) | D400 (3) + AEP (1) | NONE | 115 | 4 |
| 16 | (10) | D400 (2) + BPA (1) + AEP (1) | A (0.5) | 115 | 1.2 |
| 17 | DGEBPA (8) TMETGE (2) | T403 (3) + AEP (1) | A (0.5) | 115 | 1.9 |
| 18 | DGEBPA (12) | DETA (2.5) | B (0.5) | RT | 11 |
| 19 | (12) | TETA (2.5) | B (0.5) | RT | 13 |
| 20 | 12 | 1,2 DAP (2.5) | B (0.5) | RT | 14 |
| 21 | 12 | TREN (2.5) | B (0.5) | RT | 11 |
| 22 | 10 | T403 (4) | B (0.5) | 115 | 3.2 |
| 23 | 10 | D400 (3) + AEP (1) | B (0.5) | 115 | 2 |
| 24 | 12 | D400 (2) + AEP (1) + BPA (1) | B (0.5) | 115 | 1.25 |

DGEBPA = Diglycidyl ether of Bisphenol-A (epoxy equivalent weight of 180–195); TMETGE = trimethylol ethane triglycidyl ether; DETA = diethylene triamine; TETA = triethylene tetramine; EDA = ethylene diamine; TREN = tris (ethylene amine) amine; T403 = polyoxypropylene triamine (molecular weight 400); D400 = polyoxypropylene diamine (molecular weight 400); AEP = aminoethylpiperazine; BPA = Bisphenol-A; 1,2 DAP = 1,2-diaminopropane, RT = room temperature.

EXAMPLE 25

A hardener solution of 2.5g of aminoethylpiperazine and 0.5g of the cure accelerator of Example 1 was mixed with 10g of DGEBPA and 2g of the reaction product of cyclohexane dimethanol diglycidyl ether with carboxylic acid terminated butadiene/acrylonitrile (18% acrylonitrile in the polymer) rubber (1300×8 CTBN Hycar from BF Goodrich Co.) in 60/40 weight ratio. The resulting epoxy resin composition was applied to a steel plate in the form of a 1 mil thick coating and was cured at 100 degrees C. for 10 minutes. The resulting non-tacky, hard coating having a pencil hardness (ASTM D-3363) of 2H showed 100% adhesion (Tape Adhesion Test; ASTM D-4459) and a reverse impact strength (ASTM D-2794) of greater than 60 inch pounds.

I claim:

1. A rapid curing composition comprising a mixture of (A) a polyepoxide and an amine curing agent and (B) a thiocyanate salt of the reaction product of an alkylene polyamine and a bicyclic amide acetal.

2. The composition of claim 1 wherein the bicyclic amide acetal is one having the formula

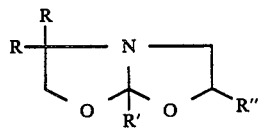

wherein R, R' and R" independently represent a hydrogen, an alkyl group having from 1 to 20 carbons, an alkyl ether group having from 1 to 20 carbon atoms, an aryl group having from 5 to 20 carbon atoms, an aryl ether group having from 6 to 20 carbon atoms, an alkaryl group having from 7 to 20 carbon atoms or an alkaryl ether group having from 7 to 20 carbon atoms.

3. The composition of claim 2 wherein the polyepoxide is a compound containing more than one group of the formula

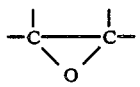

4. The composition of claim 3 wherein the alkylene polyamine is one of the formula

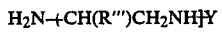

wherein R''' represents hydrogen or a methyl group, Y represents hydrogen or an aminoalkyl group having from 2 to 6 carbon atoms and n represents 1 or 2.

5. The composition of claim 3 wherein the amine curing agent is selected from the group consisting of butylamine, dodecyl amines, cyclohexylamine, ethylene diamine, diethylene triamine, triethylene tetramine, tetraethylene pentamine, propylene diamine, dipropylene triamine, bis(aminomethyl)cyclohexane, triethyl amine, tributylamine, triethylene diamine, imidazolines, imidazoles, imidazines, hexamethylene diamine, isophorone diamine, aminoethylpiperazine, bis(aminopropyl) piperazine, piperidine, piperazine, morpholine, dimer acid diamine, ethanol amine, diethanolamine, N-alkyl alkanolamines and poly(alkylene ether) polyamines of molecular weights up to 10,000.

6. The composition of claim 5 wherein the bicyclic amide acetal is one in which R and R" represent hydrogen and R' represents a methyl group.

7. The composition of claim 6 wherein the polyepoxide is the diglycidyl ether of Bisphenol-A.

8. The composition of claim 7 wherein the alkylene polyamine is 1,2-diaminopropane.

9. The composition of claim 8 wherein the amine curing agent is aminoethylpiperazine.

10. The composition of claim 7 wherein the alkylene polyamine is ethylene diamine.

11. The composition comprising a thiocyanate salt of the reaction product of an alkylene polyamine and a bicyclic amide acetal.

12. The composition of claim 11 wherein the bicyclic amide acetal is one having the formula

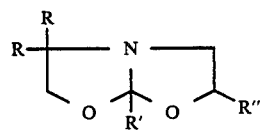

wherein R, R' and R" independently represent a hydrogen, an alkyl group having from 1 to 20 carbon atoms, an alkyl ether group having from 5 to 20 carbon atoms, an aryl ether group having from 6 to 20 carbon atoms, an alkaryl group having from 7 to 20 carbon atoms or an alkaryl ether group having from 7 to 20 carbon atoms.

13. The composition of claim 12 wherein the alkylene polyamine is one of the formula

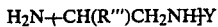

wherein R''' represents hydrogen or a methyl group, Y represents hydrogen or an aminoalkyl group having from 2 to 6 carbon atoms and n represents 1 or 2.

14. The composition of claim 13 wherein the bicyclic amide acetal is one in which R and R" represent hydrogen and R' represents a methyl group.

15. The composition of claim 14 wherein the alkylene polyamine is 1,2-diaminopropane.

16. The composition of claim 14 wherein the alkylene polyamine is ethylene diamine.

17. The process for preparing a thermoset resin comprising mixing a polyepoxide, an amine curing agent and a thiocyanate salt of the reaction product of an alkylene polyamine and a bicyclic amide acetal and curing said mixture at a temperature in the range of from about ambient to about 150° C.

18. The process of claim 17 wherein the bicyclic amide acetal is one having the formula

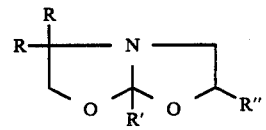

wherein R, R' and R" independently represent a hydrogen, an alkyl group having from 1 to 20 carbon atoms, an alkyl ether group having from 5 to 20 carbon atoms, an aryl ether group having from 6 to 20 carbon atoms, an alkaryl group having from 7 to 20 carbon atoms or an alkaryl ether group having from 7 to 20 carbon atoms.

19. The process of claim 18 wherein the polyepoxide is a compound containing more than one group of the formula
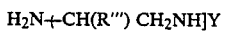
20. The composition of claim 19 wherein the alkylene polyamine is one of the formula
$$H_2N[CH(R''')CH_2NH]_nY$$
wherein R''' represents hydrogen or a methyl group, Y represents hydrogen or an aminoalkyl group having from 2 to 6 carbon atoms and n represents 1 or 2.
* * * * *